United States Patent
Imamura et al.

(10) Patent No.: US 11,353,437 B2
(45) Date of Patent: Jun. 7, 2022

(54) SAMPLE IDENTIFICATION METHOD BASED ON CHEMICAL SENSOR MEASUREMENT, SAMPLE IDENTIFICATION DEVICE, AND INPUT PARAMETER ESTIMATION METHOD

(71) Applicant: National Institute for Materials Science, Ibaraki (JP)

(72) Inventors: Gaku Imamura, Tsukuba (JP); Genki Yoshikawa, Tsukuba (JP); Takashi Washio, Suita (JP)

(73) Assignee: National Institute for Materials Science, Tsukuba (JP)

( * ) Notice: Subject to any disclaimer, the term of this patent is extended or adjusted under 35 U.S.C. 154(b) by 365 days.

(21) Appl. No.: 16/463,585

(22) PCT Filed: Nov. 22, 2017

(86) PCT No.: PCT/JP2017/042060
§ 371 (c)(1),
(2) Date: May 23, 2019

(87) PCT Pub. No.: WO2018/097197
PCT Pub. Date: May 31, 2018

(65) Prior Publication Data
US 2019/0317066 A1     Oct. 17, 2019

(30) Foreign Application Priority Data

Nov. 28, 2016 (JP) .............................. JP2016-230468

(51) Int. Cl.
*G01N 33/00* (2006.01)
*G01N 19/00* (2006.01)
(Continued)

(52) U.S. Cl.
CPC ......... *G01N 33/0027* (2013.01); *G01N 19/00* (2013.01); *G01N 29/022* (2013.01); *G01N 29/4418* (2013.01); *G01N 29/46* (2013.01)

(58) Field of Classification Search
CPC .. G01N 19/00; G01N 29/022; G01N 29/4418; G01N 29/4427; G01N 29/4472; G01N 29/46; G01N 33/0027
See application file for complete search history.

(56) References Cited

U.S. PATENT DOCUMENTS 6,091,976 A * 7/2000 Pfeiffer .............. A61B 5/14528
                                                        600/347
7,751,864 B2 * 7/2010 Buck, Jr. ............ G01N 27/3274
                                                        600/347
(Continued)

FOREIGN PATENT DOCUMENTS

| JP | H02-285248 A | 11/1990 |
| JP | 2017-156254 A | 9/2017 |
| WO | 2011/148774 A1 | 12/2011 |

OTHER PUBLICATIONS

International Search Report issued in corresponding International Patent Application No. PCT/JP2017/042060 dated Feb. 27, 2018.
(Continued)

*Primary Examiner* — Nimeshkumar D Patel
*Assistant Examiner* — Gedeon M Kidanu
(74) *Attorney, Agent, or Firm* — Morgan, Lewis & Bockius LLP

(57) ABSTRACT

Provided is a novel analysis method that enables identification of a sample even when any sample is introduced during measurement carried out by using a chemical sensor. An input in which the amount of an unknown sample changes over time is provided to the chemical sensor, a response which is from the chemical sensor and which changes over time is measured, a sensor function (transmission function)

(Continued)

of the chemical sensor with respect to the unknown sample is calculated on the basis of the input and the response, and the unknown sample is identified on the basis of the sensor function of the chemical sensor with respect to the unknown sample.

11 Claims, 9 Drawing Sheets

(51) Int. Cl.
*G01N 29/46* (2006.01)
*G01N 29/02* (2006.01)
*G01N 29/44* (2006.01)

(56) References Cited

U.S. PATENT DOCUMENTS

| | | | | |
|---|---|---|---|---|
| 2003/0186461 A1* | 10/2003 | Boehr | ............... | G01N 33/0034 73/31.02 |
| 2008/0214910 A1* | 9/2008 | Buck | ................. | A61B 5/14532 600/310 |
| 2013/0133433 A1* | 5/2013 | Yoshikawa | .......... | G01N 29/022 73/774 |

OTHER PUBLICATIONS

Potyrailo et al., "Dynamic high throughput screening of chemical libraries using acoustic-wave sensor system," Review of Scientific Instruments, 73: 1277-1283 (2002).

Wenzel et al., Sorption-induced static bending of microcantilevers coated with viscoelastic material, Journal of Applied Physics, 103: 064913 (2008).

Yoshikawa et al., "Nanomechanical Membrane-type Surface Stress Sensor," NANO Letters, 11: 1044-1048 (2011).

Nakamoto et al., "Improvement of capability for classifying odors in dynamically changing concentration using QCM sensor array and short-time Fourier transform," Sensors and Actuators B, 127: 491-496 (2007).

Marco et al., "Different strategies for the identification of gas sensing systems," Sensors and Actuators B, 34: 213-223 (1996).

Hines et al., "Electronic noses: a review of signal processing techniques," IEE Proceedings-Circuits Devices and Systems, 146: 297-310 (1999).

Nakamura et al., "Chemical sensing by analysing dynamics of plasma polymer film-coated sensors," Sensors and Actuators B, 20: 231-237 (1994).

* cited by examiner

FIG.5
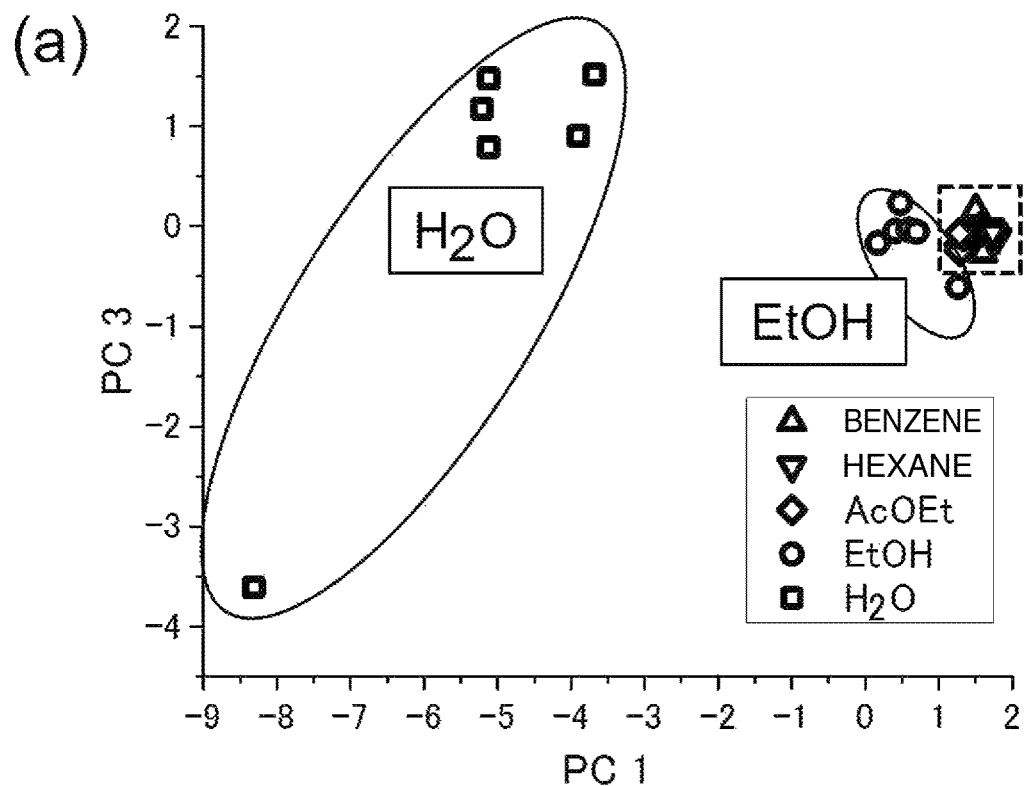
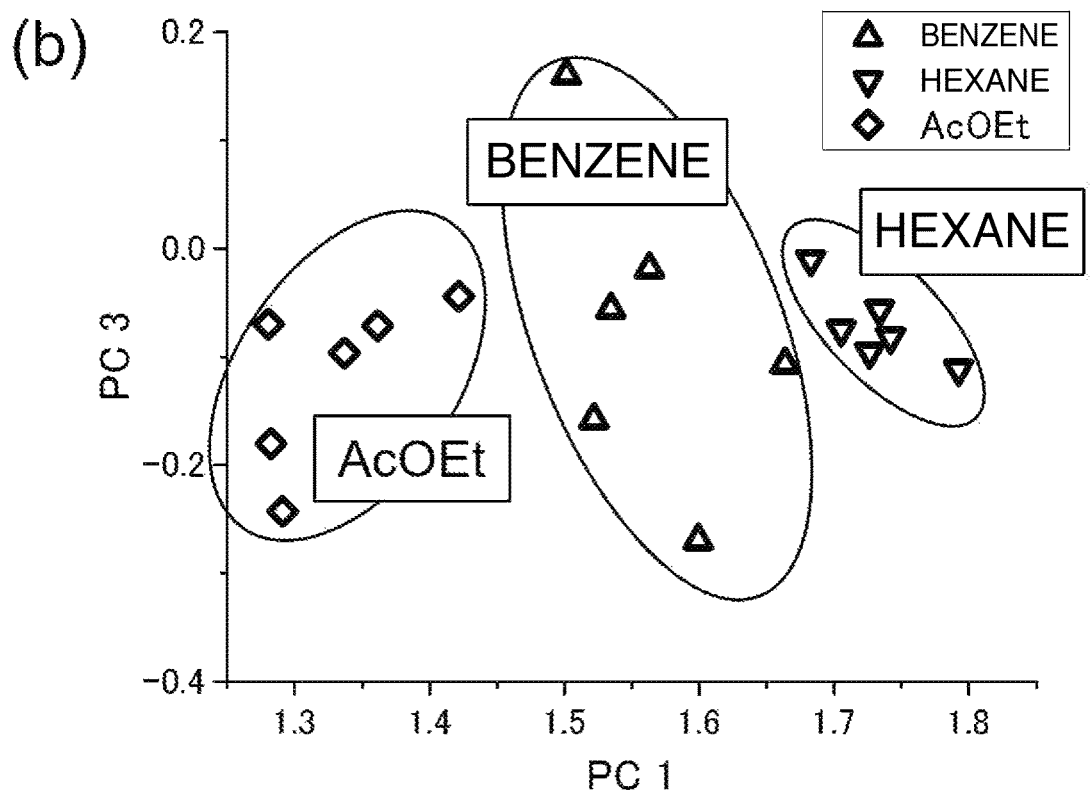

FIG.6
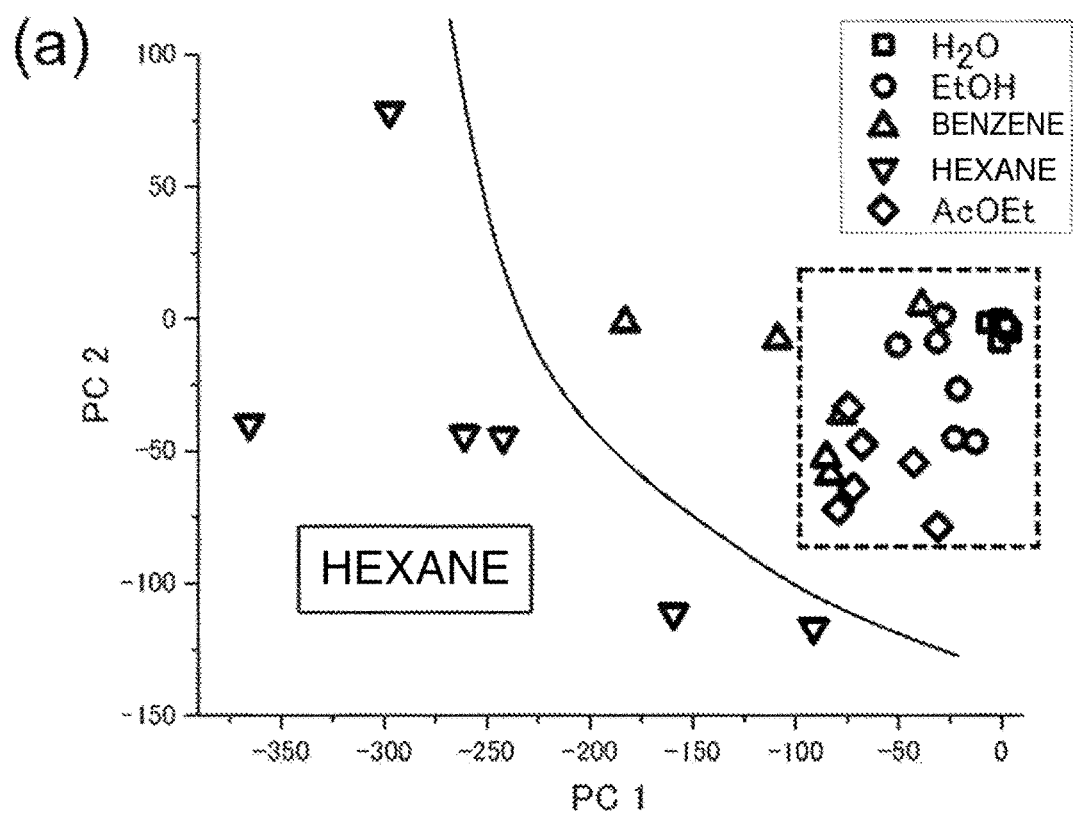
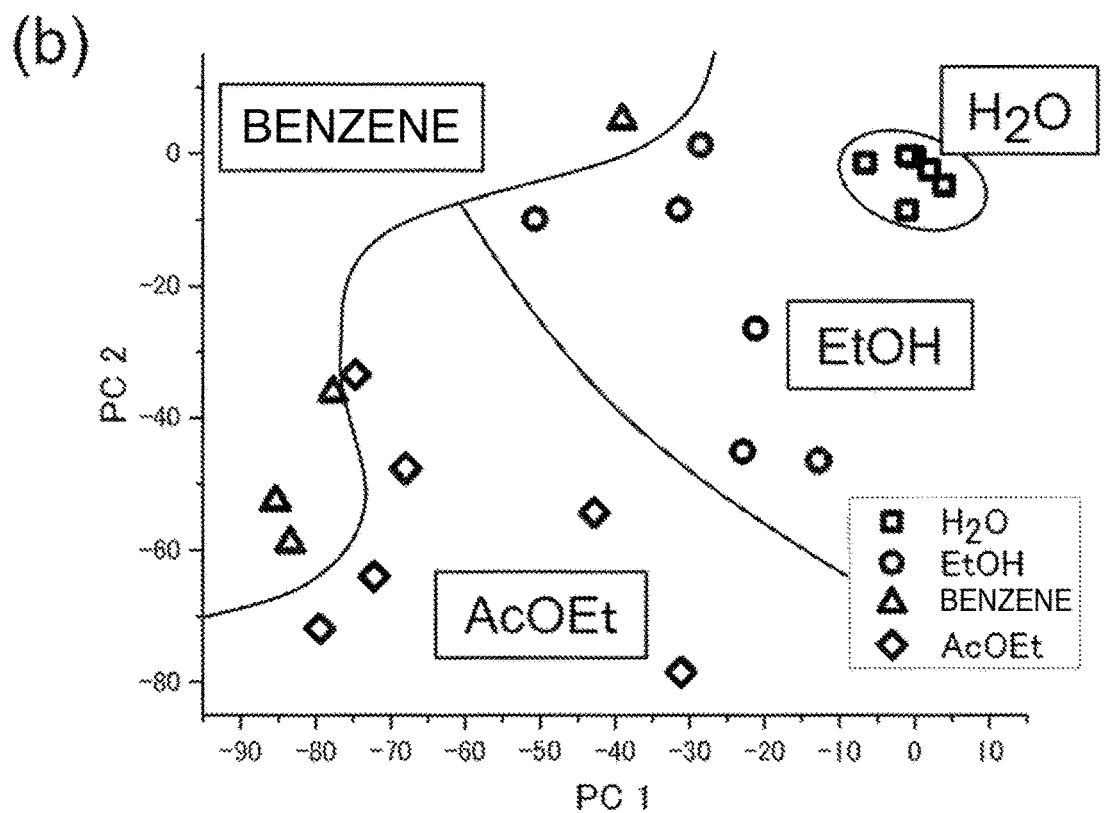

FIG.7
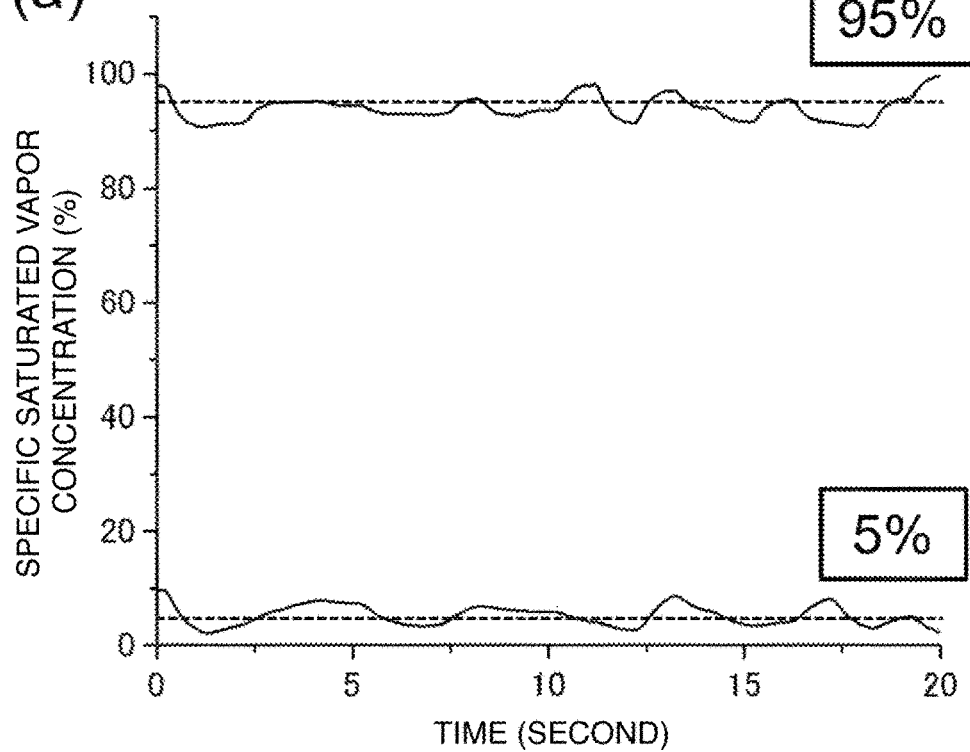
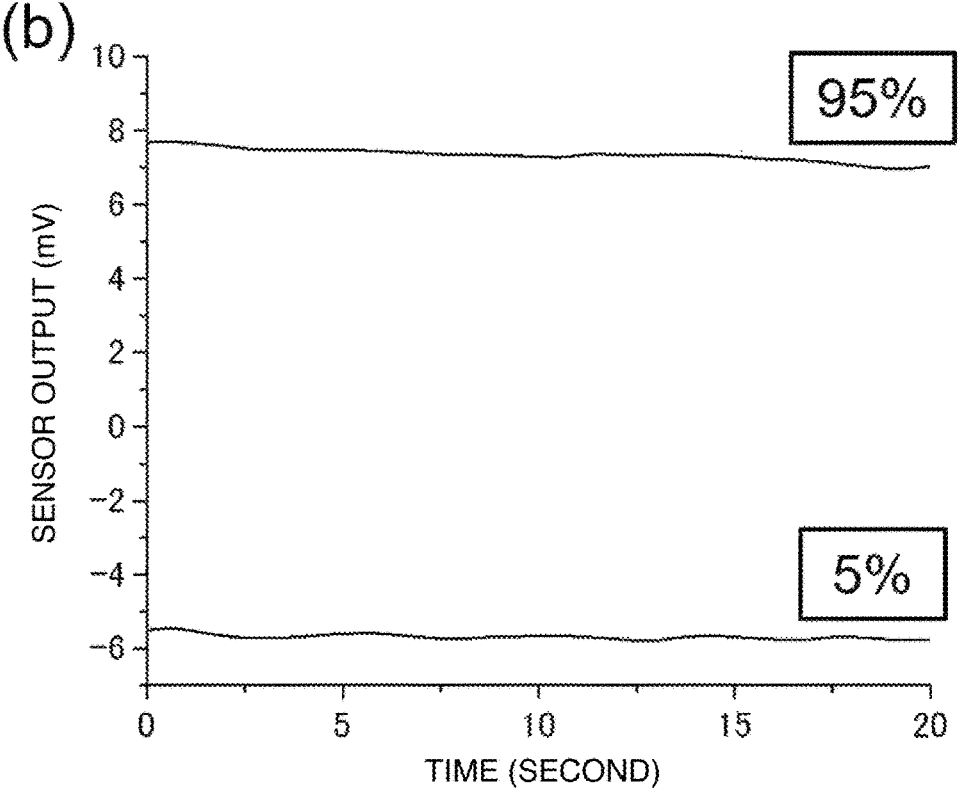

SAMPLE IDENTIFICATION METHOD BASED ON CHEMICAL SENSOR MEASUREMENT, SAMPLE IDENTIFICATION DEVICE, AND INPUT PARAMETER ESTIMATION METHOD

TECHNICAL FIELD

The present invention relates to an analysis technique in measurement in which chemical sensors are used. More particularly, it relates to a sample identification method based on transfer functions between inputs and outputs of chemical sensors. Furthermore, the present invention relates to a device which performs sample identification by such identification methods and estimation methods of parameters of the input based on the transfer function between the input to and the output from the chemical sensors. Note that needless to say, the "transfer function" mentioned in the present invention is a mathematical concept and is the same as the "transfer function" which is broadly used in the field of electronics, control engineering and so on. However, this is a term scarcely used in the field of the present invention, and hence it might give rise to a misunderstanding that this is an application of the transfer function in the field of electronics, the control engineering and so on. Thus, the "transfer function" is hereinafter called a "sensor function".

BACKGROUND ART

In analysis of a sample by chemical sensors, a variety of techniques for identification based on properties of the sample (the type, concentration, temperature and so on) exist according to the principle of the chemical sensors. In the case of sensors (e.g., a pH meter) in which their outputs specifically vary with respect to a specific chemical substance, it is possible to identify the sample according to the presence or concentration of the substance. However, in the case of chemical sensors having a wide range of selectivity, it is necessary to select and extract information which is effective for the identification from obtained sensor outputs. For example, when performing an analysis of a gas sample by using gas sensors, the gas species can be identified by extracting features from the shape of signals obtained by supplying the sample to the gas sensors. This is because interaction between the gas and the sensors differs depending on the gas species, leading to signals with different shapes for each gas species. However, to identify the gas species from the sensor signals in this manner, the gas always needs to be supplied to the sensors with the same manner. For example, even from the same gas, the shapes of sensor signals are different between the case where a sample gas is supplied at a constant flow rate from a certain time and the case where the sample gas is introduced by gradually increasing a flow rate from a certain time. Therefore, data obtained through different gas supplying methods cannot be compared with each other.

In contrast, there is also a technique of performing the identification of the sample by building a model based on a theoretical model for extracting common parameters from measurement results. For example, in Non Patent Literature 1, a theoretical model is constructed for a cantilever-type sensor covered with viscoelastic materials, and the parameters are extracted from the measurement results by solving differential equations which contain the supply of the sample (temporal change of the concentration). In this case, in principle, the parameters can be extracted from the shape of the obtained sensor signals for any type of gas supply method, and evaluation of the parameters enables the gas identification. However, this technique is valid only in a system which matches the model, giving rise to severe restriction on systems to which the technique is adapted.

Therefore, a sensor signal analysis method which is adaptable to any sensor and does not limit the supplying method of samples has been required. For that purpose, a research has been reported where the concentration of the sample is randomly changed, and the sample is then supplied to the sensor, followed by an analysis based on the frequency components of the obtained signals. Although the supply of samples differs for every measurement, this technique is based on the principle that the random supply of the gases contains various frequency components. Thus, in the gas supplying method, random inputs need to contain uniform frequency components for analysis; hence, the input is also considered to be limited in this technique. In addition, there is an analytical approach in which a concept of control engineering is introduced; a gas measurement setup is considered as a system consisting of a sample supply to the sensors and sensor signals considered as an input as an output, respectively. For example, according to Non Patent Literatures 4 and 5, a sensor measurement system is considered as a system where gas concentration change and sensor signals are an input and outputs, respectively, and the relationship between them are estimated in these studies. However, these approaches mainly focus on predicting the concentration change from the relationship between inputs and outputs, and there are only few approaches in which the gas identification is performed. In Non Patent Literature 6, an autoregressive (AR) model is estimated from the relationship between inputs and the output, and the gas species is identified based on the relationship, but the gas supply, which is considered as an input in the AR model, needs to be fixed, resulting in the restriction of the sample supply.

CITATION LIST

Patent Literature

PATENT LITERATURE 1: WO 2011/148774

Non Patent Literature

NON PATENT LITERATURE 1: M. J. Wenzel, F. Josse, S. M. Heinrich, E. Yaz, and P. G. Datskos, "Sorption-induced static bending of microcantilevers coated with viscoelastic material" Journal of Applied Physics 103, 064913 (2008).

NON PATENT LITERATURE 2: G. Yoshikawa, T. Akiyama, S. Gautsch, P. Vettiger, and H. Rohrer, "Nanomechanical Membrane-type Surface Stress Sensor" Nano Letters 11, 1044-1048 (2011).

NON PATENT LITERATURE 3: N. Nimsuk, T. Nakamoto, "Improvement of capability for classifying odors in dynamically changing concentration using QCM sensor array and short-time Fourier transform" Sensors and Actuators B: Chemical 127, 491-496 (2007).

NON PATENT LITERATURE 4: S. Marco et al., "Different strategies for the identification of gas sensing systems" Sensors and Actuators B: Chemical 34, 213-223 (1996).

NON PATENT LITERATURE 5: E. L. Hines, E. Llobet, J. W. Gardner "Electronic noses: a review of signal processing techniques" IEE Proceedings-Circuits Devices and Systems 146, 297-310 (1999).

NON PATENT LITERATURE 6: M. Nakamura, I. Sugimoto, H. Kuwano, R. Lemos, "Chemical sensing by analysing dynamics of plasma polymer film-coated sensors" Sensors and Actuators B: Chemical 20, 231-237 (1994).

SUMMARY OF INVENTION

Technical Problem

The object of the present invention is to provide a novel analysis method and a device that enable identification of samples by chemical sensors even when the samples are supplied through an arbitrary method.

Solution to Problem

According to one aspect of the present invention, a sample identification method by means of a chemical sensor measurement is provided wherein time-varying input of an unknown sample is provided to a chemical sensor, a time-varying response measured from the chemical sensor, a sensor function of the chemical sensor is derived on the unknown sample based on the input and the response, and the unknown sample is identified based on the sensor function of the chemical sensor on the unknown sample.

Here, the sensor function can be a sensor function the basis of which is transformed into any basis other than time.

Furthermore, the sensor function can be a time-basis sensor function.

Furthermore, the time-basis sensor function can be obtained by performing fitting so as to provide the measured response from the input.

Furthermore, the transformation of the basis can be performed by orthogonal transformation or pseudo-orthogonal transformation.

Furthermore, the orthogonal transformation or the pseudo-orthogonal transformation can be a transformation that transforms convolution into multiplication.

Furthermore, the identification of an unknown sample based on a sensor function of a chemical sensor can be performed by a comparison with a sensor function on one or more known samples obtained separately.

Furthermore, the variation range of the amount of the sample in the input supplied to the chemical sensor can be limited to a predetermined range in order to obtain the sensor function of the chemical sensor with respect to the unknown sample.

According to another aspect of the present invention, a sample identification device is provided which performs identification of an input sample by using any of the aforementioned sample identification methods by means of chemical sensor measurement, comprising means for supplying a time-varying amount of the unknown sample to a chemical sensor, and means for receiving the time-varying response signal from the chemical sensor.

According to still another aspect of the present invention, a method for estimating a parameter of an input by means of chemical sensor measurement is provided, wherein an input with a time-varying amount is provided to a chemical sensor, a time-varying response is from the chemical sensor is measured, a sensor function of the chemical sensor on an unknown sample is obtained based on the input and the response, and a value of a parameter that changes the sensor function is obtained based on the sensor function of the chemical sensor on the unknown sample, wherein the parameter is a parameter of the input to the chemical sensor.

Here, the parameter can be a temperature of the input to the chemical sensor or a concentration of the sample contained in the input to the chemical sensor.

Advantageous Effects of Invention

According to the present invention, a sample can be analyzed by a "sensor function", that is the relationship between a sample supply and signals obtained from chemical sensors by considering them as an input and an output, respectively. Thus, identification based on the properties of a sample becomes possible for any sample input.

BRIEF DESCRIPTION OF DRAWINGS

FIG. 5 is (a) the result of principal component analysis performed on the frequency-domain sensor functions obtained through each measurement in Example 1. (b) is an enlarged view of the dotted region in (a).

FIG. 6 is the result of principal component analysis performed on the discrete time finite response sensor functions obtained through each measurement. (b) illustrates an enlarged view of the dotted region in (a).

FIG. 7 is (a) the flow rates of MFC1, and (b) responses of the sensor for the measurements of water vapor at different concentrations in Example 2.

DESCRIPTION OF EMBODIMENTS

In one aspect of the present invention, a technique for analyzing samples is provided that is performed by obtaining sensor functions from flow rates as inputs and sensor signals as outputs when supplying the samples into chemical sensors. Thus, an identification technique based on sample properties (gas species, concentration, temperature, pressure and so on) is provided.

In the present invention, sample analysis is performed by means of measurements with chemical sensors. Therefore, there are no special restrictions on the structure, operating principle or others of sensors which are usable in the present invention as long as they show any responses to samples. Note that samples are not limited to gaseous samples; liquid samples are also measurable.

(Theoretical Background)

Figure 1:
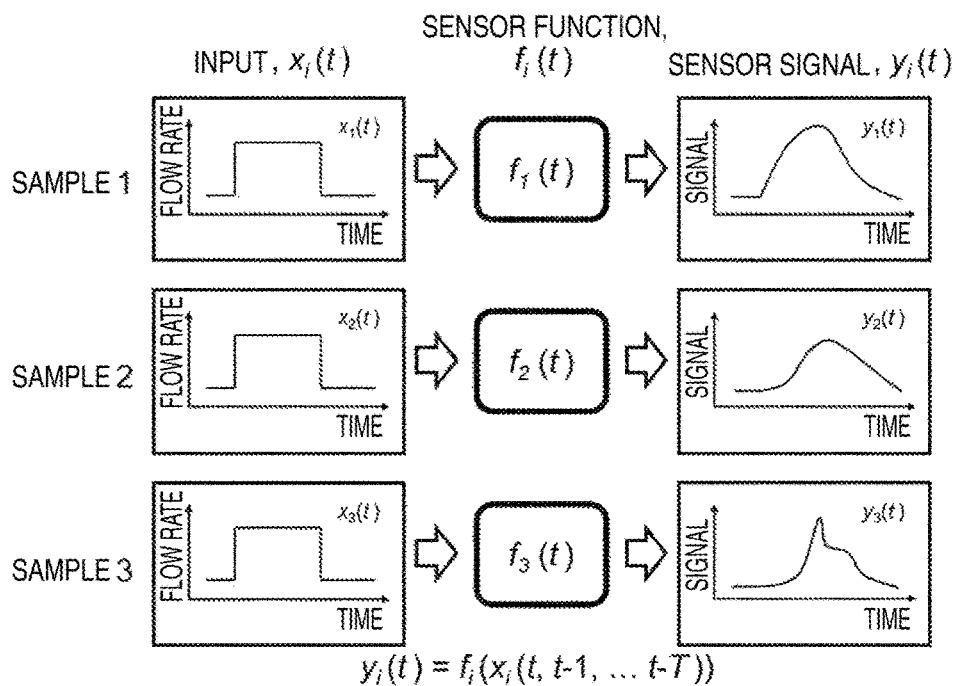
FIG. 1 is a conceptual diagram showing the relation between inputs of samples, outputs obtained from chemical sensors and sensor functions, which connect them in the time domain in the case of samples i (i=1 to 3) are measured by sensors.

FIG. 1 illustrates a conceptual diagram of the present invention. When a sample is supplied to a chemical sensor, a signal is obtained according to the operating principle of the chemical sensor. Now this sample supply is considered as an input, and the obtained signal is considered as an output. At this time, the function that describes the relationship between the input and the output is defined as the "sensor function". In general, when the sample is analyzed by using the chemical sensor, the sample is analyzed by processing the signals. However, in the present invention, the signal is not the main focus, but the sensor function is used for the analysis. The relationship between the input and the output changes in accordance with properties of the sample (species, concentration, temperature, pressure and so on); hence, sample analysis becomes possible by focusing on the sensor functions, which connects both the input and the output.

As an example, a system where the relation between the input and the output is linear is considered. First, as illustrated in FIG. 1, the inflow of samples i (i=1 to 3) into a sensor device $x_i(t)$ is considered as the input, and the resultant sensor signal $y_i(t)$ is considered as the output. Note that t denotes time. Now, as the relationship between $x_i(t)$ and $y_i(t)$ is assumed to be linear, $y_i(t)$ can be represented as the following convolution by using the time-domain sensor function $h_i(t)$:

[MATH. 1]

$$y_i(t)=\int_0^t h_i(\tau)x_i(t-\tau)d\tau=h_i(t)*x_i(t) \quad (1)$$

Generally, in convolution integral, the integration interval is from $-\infty$ to $+\infty$. However, as $x_i$ after a time t does not have any influence on current $y_i$ due to causality, $\tau<0$ is excluded from the integration interval for $\tau$. It is also assumed that measurement is performed for a time sufficiently longer than the time required for signal transfer from $x_i$ to $y_i$, and that the influence of $x_i$ before the start time t=0 on the current $y_i$ can be ignored, leading to the exclusion of the time region $t-\tau<0$, that is $\tau>t$, from the integration interval of $\tau$. As a result, the integration interval is [0:t].

This time-domain sensor function $h_i(t)$ does not depend on the inflow of the sample i $x_i(t)$ as long as it is a linear system, whereas the function differs depending on properties of the sample i. Thus, sample analysis becomes possible based on the time-domain sensor function $h_i(t)$, which is obtained from the inflow $x_i(t)$ as the input and the sensor signal $y_i(t)$ as the output.

Next, the input and output in the frequency domain are considered. The time-domain input $x_i(t)$, output $y_i(t)$ and sensor function $h_i(t)$ can be expressed as $X_i(f)$, $Y_i(f)$ and $H_i(f)$, respectively, as functions of frequency f by applying Fourier transform or Laplace transform. At this time, $X_i(f)$ and $Y_i(f)$ can be described by using a frequency-domain sensor function $H_i(f)$ as follows:

[MATH. 2]

$$Y_i(f)=H_i(f)X_i(f) \quad (2)$$

As the frequency-domain sensor function $H_i(f)$ also differs depending on the properties of the sample i, sample analysis is possible with $H_i(f)$ obtained by measurements. Note that Equations (1) and (2) are representations in the time domain and the frequency domain, respectively, and that the two equations are mathematically equivalent.

Furthermore, when $h_i(t)$ or $H_i(f)$ is known from Equation (1) or Equation (2), the input $x_i(t)$ or $X_i(f)$ can be estimated from the obtained sensor signal $y_i(t)$ or $Y_i(f)$.

Note that actual measurement systems are not strictly linear in many cases. However, if an error caused by deviation from this linearity falls within a range permitted according to the purpose of the measurement, such a system can be regarded as linear, and the measurement can be performed by the present invention. Furthermore, even in a measurement system where large nonlinearity appears in the whole range of parameter for the input (e.g., the concentration of a target substance) during the measurement, the present invention is adaptable by regarding the system as a linear system for the following cases; the case where the parameter varies within the range in which the system is sufficiently linear—"piecewise linearity"—, or the case where an approximate value (the range at which the actual value is) is known or estimated through another method even though the parameter varies in a large range. It should be noted that the present invention includes a case where the system has such slight nonlinearity or the piecewise linearity. One can achieve this, for example, by obtaining a sensor function by limiting the range of the parameter such as input concentration to chemical sensors in the range where the linearity is ensured, or by dividing the range of the parameter into multiple ranges in which linearity is ensured and then changing the parameter in each divided range.

Moreover, also in the case where the nonlinearity described above is remarkable, the value of the parameter on the input (e.g., the concentration in such a case as described above) can be reversely obtained if the substance to be inputted into the measurement system is known.

Furthermore, when there is a parameter which does not apparently appear in $h_i(t)$ or $x_i(t)$ but has an actual influence on the system behavior, a value of such a parameter can be obtained if the substance is known. For example, in the case where the time sensor function varies with temperature, the corresponding temperature range can be estimated by deriving the time-domain sensor function (or the frequency-domain sensor function) if the time-domain sensor function in each temperature range is checked in advance.

Additionally, in the above theoretical description, the inflow of the sample to a sensor device is used as the input of the measurement system in Equation (1), but any possible parameter as an input in chemical sensor measurement can be adopted as the input.

In addition to principal component analysis used in Examples, pattern recognition techniques and other discrimination techniques can be used to identify a sample from the sensor function derived from measurements; based on the sensor function (e.g. the vector consisting of a values of functions at each frequency as shown in the table in Examples), it is possible to evaluate the cluster the sample belongs to or how close the sample is to the samples that are measured beforehand.

In the above description, the sensor function h(t) is obtained from the input x(t) and the output y(t) as H(f) through Laplace transform or Fourier transform as illustrated in FIG. 1. However, it should be noted that Laplace transform or Fourier transform is not necessarily required to be used, or this transformation does not need to be represented as the function of the frequency domain. This transformation can be any transformation that convert the basis of the time sensor function h(t) into another basis other than time. As illustrated in FIG. 1, the sensor function can be any function f that is described in the general form $y(t)=f(x(t, t-1, \ldots, t-T))$ (T is equal to or more than zero and finite), which transforms input time series to sensor x(t) to the output sensor time series y(t). As this transformation, orthogonal transformation or pseudo-orthogonal transformation is preferably used. More preferably, transformation that transforms convolution into multiplication (Equation (2)) such as Laplace transform or Fourier transform is used.

Furthermore, the time sensor function h(t) can be obtained directly from the relationship between the input x(t) and the output y(t) without performing the aforementioned basis transformation. As a nonrestrictive example of technique to achieve this, the output y(t) is measured with respect to the input x(t), and the time-domain sensor function h(t) can be obtained by performing fitting so that both the input and the output satisfy the above relationship described as Equation (1). Details will be described in the latter half of the description of Example 1.

If f is a nonlinear function, there is a possibility that the function f is not necessarily uniquely determined with respect to the same set of the input time series x(t) and the output time series y(t); multiple local solutions can exist. If the function is not uniquely determined—multiple possible combinations of the parameter values of f (e.g., refer to series of sensor function values at every frequency point in Example 1) exist, it is required to evaluate the gas species or concentration of the sample by the following procedure: all possible combinations are found for each sample beforehand, and a set of the parameter values of the function f for an unknown sample is estimated. If the set of the parameter values of the unknown samples matches or is close to a combination, then the gas species or the concentration of the sample can be determined according to the corresponding set of the parameter values. This is possible when all the possible combinations for each sample can be found. It depends on which function f represents the sensor or which mathematical properties the function f has whether finding all the combinations beforehand through experiments is possible or not. Therefore, it is difficult to obtain all of them through the experiments beforehand, when there is no restriction on the function f.

When the function f is restricted to a linear function, the sensor function is uniquely determined (i.e., there is only one set of parameter values), making it easier to handle mathematically.

Hereinafter, the present invention will be further described in detail on the basis of examples. However, needless to say, the present invention is not limited to these examples. For example, a membrane-type surface stress sensor (MSS) (Patent Literature 1 and Non Patent Literature 2) will be used below as an example of the chemical sensor. However, a chemical sensor other than MSS can be used depending on conditions.

Example 1

(Identification of Gas Species Based on Sensor Function)

In the present example, measurement of head space gases of solvents was performed by using MSS, and the gas species were identified.

Figure 2:
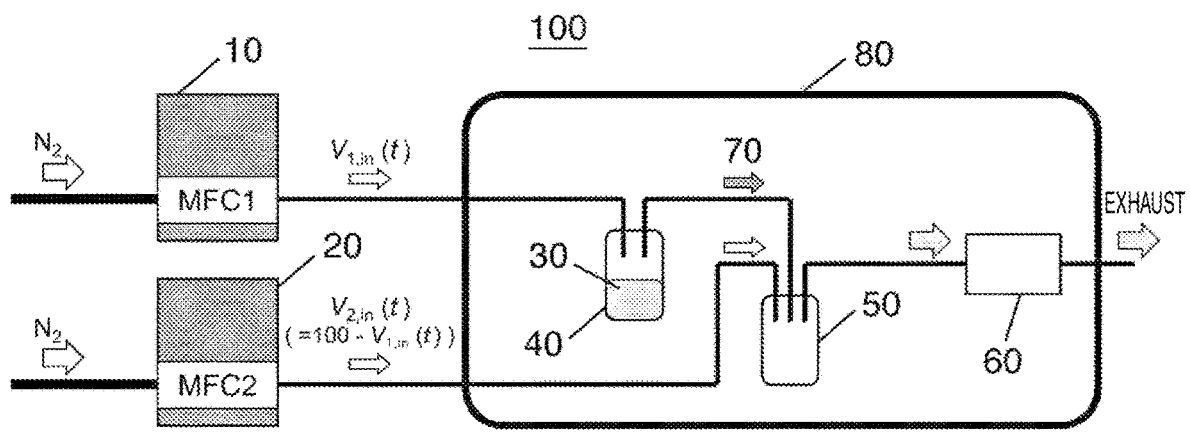
FIG. 2 is a schematic illustration of a flow path of a gas for the measurements in Example 1.

FIG. 2 illustrates a schematic illustration of the experimental system 100 used in the present example. A nitrogen gas was supplied from the two mass flow controllers (MFC) 10 and 20, and one MFC (MFC1) 10 was connected to a vial 40 in which a solvent 30 was contained as a sample. The vial 40 containing solvent 30 was also connected to another empty vial 50, and the other MFC (MFC2) 20 was directly connected to this empty vial 50. This empty vial 50 was also connected to a sensor chamber 60 in which the MSS was set, and a gas passed through the sensor chamber 60 was exhausted thereafter. According to this experimental system, a head space gas 70 can be supplied to the sensor by changing the concentration of the gas. As a saturated vapor pressure differs depending on the types of solvent, concentration ratio of a vapor to its saturation vapor $x_i$ is used as an input here. For example, in the case that water ($H_2O$) is used as the solvent, when a flow rate of MFC1 10 is 30 sccm and a flow rate of MFC2 20 is 70 sccm, the concentration ratio $x_{H2O}$ of water is 30%. The MSS was covered with polymethylmethacrylate (PMMA) as a receptor layer to gases. The vial and the sensor chamber were placed in an incubator, and the temperature was fixed at a constant value (25° C.).

Figure 3:
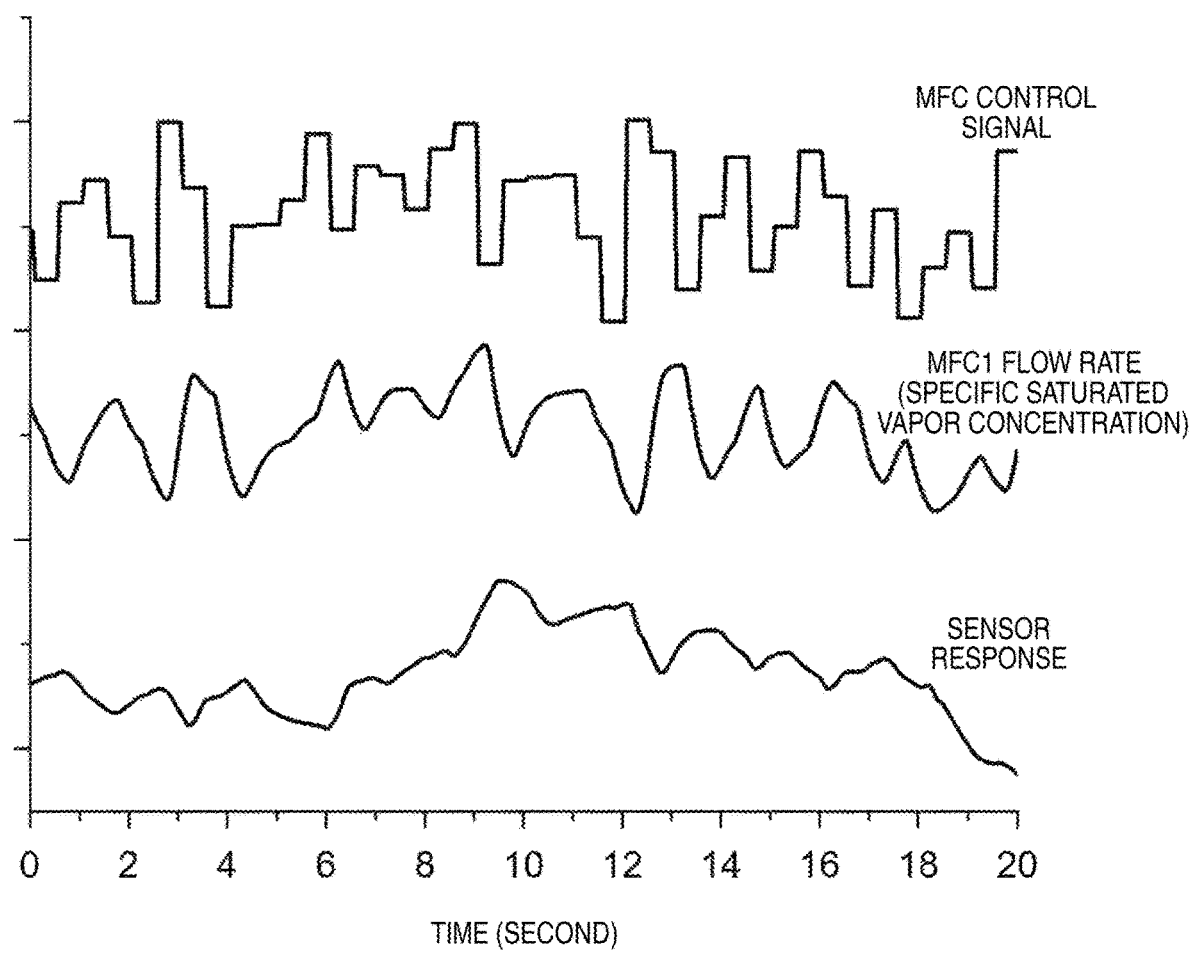
FIG. 3 shows a control signal of the mass flow controller (MFC), the flow rate (a measured value) of MFC1 and a signal of the sensor in Example 1.
Figure 4:
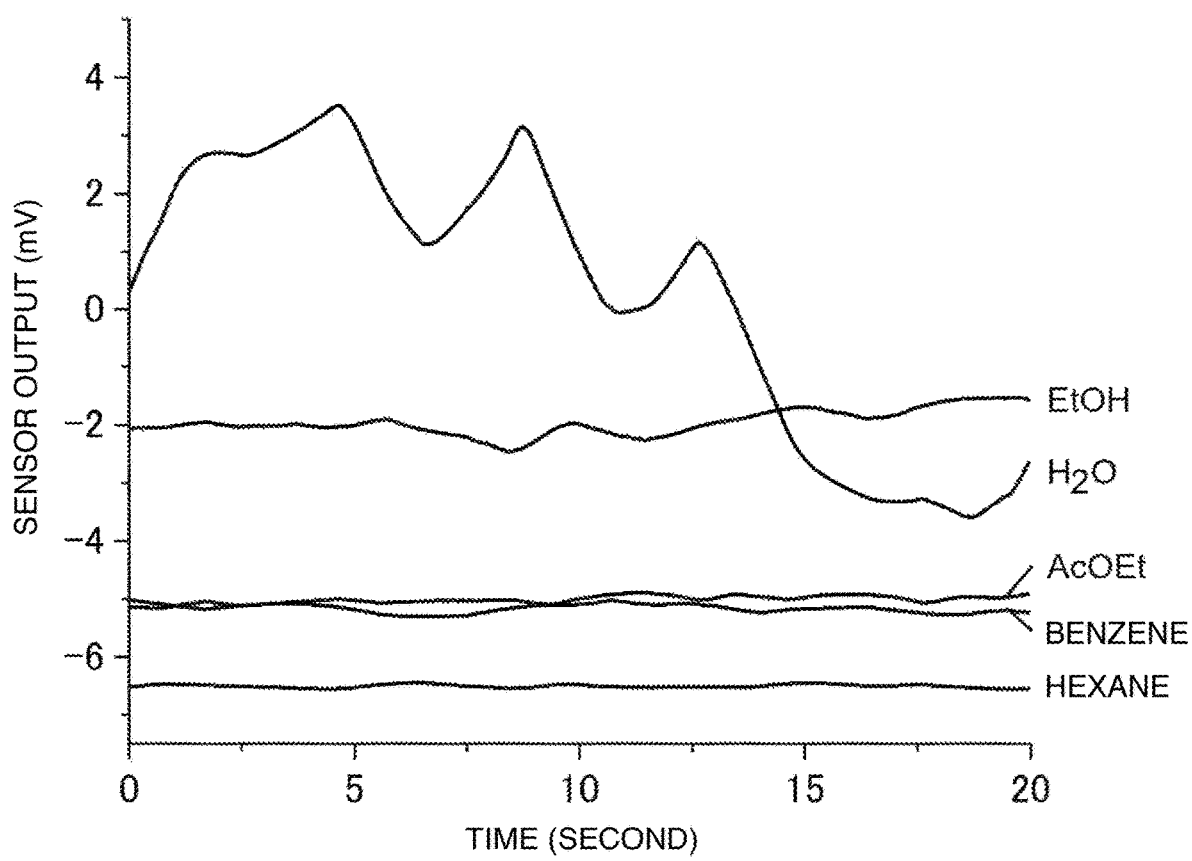
FIG. 4 shows the sensor signals for the measurements of water ($H_2O$), ethanol (EtOH), benzene, ethyl acetate (AcOEt) and hexane in Example 1.

In the present example, the flow rate was randomly changed at MFC1 10, and the flow rate (actual measurement) of MFC1 10 and signals of the sensor were measured. In principle, a frequency-domain sensor function can be obtained by providing an impulse (a pulse having infinitely small temporal width and infinitely large height) as an input and observing a response to the input. However, it is difficult to provide such an impulse in an actual experimental system. Moreover, it is difficult to extract only a response to the impulse from an output signal in the case where noise exists in the output. To solve the problem, in the present example, white noise instead of the impulse was provided as the input to obtain frequency-domain sensor functions. As the white noise shows a constant value at every frequency, it is possible to obtain the frequency-domain sensor function by evaluating the response to the white noise. However, as will be described later, in the analysis method provided by the present invention, the input needs to contain only the frequency components used in this analysis, and the components does not need to be uniform. Therefore, it should be noted that the input is not limited to a random input. As the frequency at which the input can be controlled is finite in an actual experimental system, frequency component up to the half of the input frequency can be evaluated according to Nyquist theorem. In the present example, as illustrated in FIG. 3, the flow rate of MFC1 10 was randomly changed in a range from 0 to 100 sccm at every second (1 Hz). When the flow rate of MFC1 was $V_{1,in}(t)$ sccm, a flow rate $V_{2,in}(t)$ of MFC2 20 was set to $V_{2,in}(t)=100-V_{1,in}(t)$ sccm so that the sum of the flow rates of MFC1 10 and MFC2 20 was always 100 sccm. A measurement time was set to 20 seconds per measurement, and 400 sampling points of data were obtained at a sampling frequency of 20 Hz (every 0.05 second from 0 second to 19.95 seconds). As samples, five types of solvents, namely, water, ethanol (EtOH), benzene, ethyl acetate (AcOEt) and hexane were used, and measurement was performed for six times for each solvent. FIG. 4 illustrates a measurement example of each solvent.

From the measurement results, the frequency-domain sensor function was obtained for analysis by using the concentration ratio (linear with respect to the measured flow rate value of MFC1) as the input and the sensor signals as the output. First, Fourier transform was applied to the measurement data to obtain the frequency components of the concentration ratio and the sensor signals. Next, the frequency-domain sensor functions can be calculated by dividing the frequency components of the sensor signals by the frequency components of the concentration ratio. As the measurement was performed for 20 seconds (400 points) at a sampling frequency of 20 Hz in the present example, the frequency increment was 0.05 Hz. As the flow rate was randomly changed at every second (1 Hz) in the present example, the frequency components up to 0.5 Hz, that is a half of 1 Hz, are effective in the analysis according to Nyquist theorem. Note that as described above, the frequency at which the input can be controlled has an upper limit in an actual device due to the limitation including response speed of MFC in the present example; the system could scarcely follow the input when the flow rate was switched at a frequency higher than 1 Hz. In consequence, the frequency-domain sensor function was evaluated by using 10 components: 0.05, 0.1, 0.15, . . . , 0.5 Hz. Thus, the frequency-domain sensor function is obtained as a 10-dimensional complex vector for a measurement.

Tables 1 to 3 summarize the calculated sensor functions for water, ethanol, benzene, hexane, tetrahydrofuran (THF) and ethyl acetate. Note that THF in the tables was a solvent used in Example 4, and a frequency-domain sensor function of the solvent was obtained in the same manner as five solvents described above. In addition, it should be noted that even though a frequency-domain sensor function $H_i(f)$ is the function of the frequency, numeric values shown in the tables are values (complex numbers) of the frequency-domain sensor functions at 10 frequencies every 0.05 Hz from 0.05 Hz to 0.5 Hz as described above.

TABLE 1

| Transmission | | 1st time | | 2nd time | | 3rd time | |
|---|---|---|---|---|---|---|---|
| function list | | Real part | Imaginary part | Real part | Imaginary part | Real part | Imaginary part |
| $H_2O$ | 0.05 Hz | 1.0328E−01 | −5.5599E−02 | 1.1622E−01 | −5.9880E−02 | 6.0409E−02 | −4.2966E−02 |
| | 0.1 Hz | 5.9180E−02 | −9.0493E−02 | 2.1625E−02 | −7.9253E−02 | 1.1289E−02 | −6.4757E−02 |
| | 0.15 Hz | 1.7468E−02 | −1.0942E−01 | −2.7242E−03 | −5.1149E−02 | 6.9455E−03 | −5.2844E−02 |
| | 0.2 Hz | 4.9289E−03 | −2.1831E−02 | 1.1892E−02 | −4.0342E−02 | −8.2124E−03 | −4.8288E−02 |
| | 0.25 Hz | −9.3281E−03 | −4.5799E−02 | −1.0543E−02 | −2.3870E−02 | −9.9339E−03 | −2.5344E−02 |
| | 0.3 Hz | 1.4613E−02 | −3.5980E−02 | 2.4012E−03 | −2.9943E−02 | −9.7401E−03 | −2.9779E−02 |
| | 0.35 Hz | 2.2419E−02 | −5.0493E−02 | −1.6264E−02 | −2.0280E−02 | −1.1035E−02 | −1.6873E−02 |
| | 0.4 Hz | −7.0014E−03 | −6.4033E−02 | −1.5818E−02 | −1.1742E−02 | −1.7358E−02 | −2.0721E−02 |
| | 0.45 Hz | −7.8596E−02 | 1.3399E−02 | −1.4134E−02 | −1.3863E−02 | −5.7321E−03 | −1.2595E−02 |
| | 0.5 Hz | −1.5103E−02 | −4.5857E−02 | −7.4989E−03 | −8.9104E−03 | −1.4073E−02 | −1.3782E−02 |
| EtOH | 0.05 Hz | 2.0394E−02 | −2.1968E−03 | −2.7051E−02 | 1.0271E−02 | 1.3781E−02 | −6.3873E−03 |
| | 0.1 Hz | −1.1502E−02 | −1.8257E−02 | 1.2501E−03 | −2.0939E−02 | 5.8347E−04 | −1.2508E−02 |
| | 0.15 Hz | 1.4712E−02 | −7.1393E−03 | 3.4820E−03 | −5.7706E−03 | 6.6234E−03 | −7.7295E−03 |
| | 0.2 Hz | 5.5971E−03 | −9.1515E−03 | 3.5052E−03 | −3.0363E−03 | 1.9000E−03 | −6.2345E−03 |
| | 0.25 Hz | −1.8462E−03 | −7.3133E−03 | 9.6014E−04 | −5.9610E−03 | 4.5880E−04 | −8.4854E−03 |
| | 0.3 Hz | 1.1386E−02 | −1.2809E−02 | 3.2415E−03 | −1.0879E−02 | −8.3229E−03 | −9.1603E−03 |
| | 0.35 Hz | −3.0697E−03 | −3.9774E−03 | 5.9717E−04 | −5.6314E−03 | −4.0858E−03 | −8.4386E−03 |
| | 0.4 Hz | 3.2209E−03 | −5.1378E−03 | 1.9788E−03 | −1.5192E−03 | −7.3209E−04 | −9.3970E−04 |
| | 0.45 Hz | −2.5247E−03 | −3.8899E−03 | 1.8297E−04 | −2.4984E−03 | −1.8088E−03 | −4.5183E−03 |
| | 0.5 Hz | −7.3010E−04 | −4.9992E−03 | 2.5201E−03 | −6.3821E−03 | −1.8558E−03 | −4.3059E−03 |
| Transmission | | 4th time | | 5th time | | 6th time | |
| function list | | Real part | Imaginary part | Real part | Imaginary part | Real part | Imaginary part |
| $H_2O$ | 0.05 Hz | 8.0571E−02 | −6.8089E−02 | 9.0176E−02 | −9.6259E−02 | 6.7365E−02 | −9.6807E−02 |
| | 0.1 Hz | 2.7865E−02 | −8.5605E−02 | 3.0000E−02 | −7.4056E−02 | 3.9922E−03 | −1.1334E−01 |
| | 0.15 Hz | 8.8054E−03 | −1.0105E−01 | −2.5077E−04 | −3.9676E−02 | 6.4590E−03 | −8.9231E−02 |
| | 0.2 Hz | −2.2351E−03 | −3.7540E−02 | −4.6282E−03 | −3.3012E−02 | −8.5109E−03 | −3.6460E−02 |
| | 0.25 Hz | 6.5647E−03 | −3.4320E−02 | −4.4575E−03 | −4.2504E−02 | 3.5226E−03 | −2.3289E−02 |
| | 0.3 Hz | −9.9000E−03 | −1.9872E−02 | −1.0037E−02 | −2.7472E−02 | −9.2597E−03 | −2.8825E−02 |
| | 0.35 Hz | −2.5165E−02 | −5.2831E−02 | −2.0684E−02 | −1.2705E−02 | −1.0425E−02 | −1.8717E−02 |
| | 0.4 Hz | −1.4423E−02 | −1.3472E−02 | −1.0404E−02 | −2.0285E−02 | −9.1287E−03 | −1.9539E−02 |
| | 0.45 Hz | −1.0697E−02 | −1.0879E−02 | 4.2424E−02 | 7.0458E−02 | −2.0578E−02 | −1.0373E−03 |
| | 0.5 Hz | −4.8395E−03 | −7.5125E−03 | −9.6240E−03 | −1.6307E−02 | −1.3891E−02 | −2.1317E−02 |
| EtOH | 0.05 Hz | 1.4233E−02 | −1.7910E−02 | 2.0241E−02 | −1.7331E−02 | 1.6281E−02 | −9.2170E−03 |
| | 0.1 Hz | 2.9005E−03 | −3.4825E−03 | 8.1371E−03 | −1.5113E−02 | 1.3268E−02 | −2.0537E−02 |
| | 0.15 Hz | 4.8950E−03 | −1.0052E−02 | 5.0402E−03 | −1.2352E−02 | 3.5577E−03 | −1.3131E−02 |
| | 0.2 Hz | 2.4900E−03 | −7.8438E−03 | 5.9465E−04 | −9.9951E−03 | 1.5769E−03 | −8.3098E−03 |
| | 0.25 Hz | −8.3839E−04 | −7.0734E−03 | −5.3573E−04 | −6.6532E−03 | 7.8555E−04 | −8.6614E−03 |
| | 0.3 Hz | 7.3715E−04 | −7.3797E−03 | −1.6770E−03 | −8.8714E−03 | −1.2746E−03 | −6.8083E−03 |
| | 0.35 Hz | −4.1986E−04 | −8.2236E−03 | 3.9622E−04 | −5.5443E−03 | −3.9310E−03 | −1.7881E−02 |
| | 0.4 Hz | 2.9286E−05 | −3.9774E−03 | −2.8724E−03 | −4.4432E−03 | −1.4748E−03 | −5.2929E−03 |
| | 0.45 Hz | −1.0801E−02 | −2.2375E−02 | 2.7869E−03 | −4.0004E−03 | −3.1101E−03 | −5.2847E−03 |
| | 0.5 Hz | −1.6382E−03 | −4.1103E−03 | −2.0664E−03 | −2.2079E−03 | −1.1640E−03 | −2.5744E−03 |

TABLE 2

| Transmission | | 1st time | | 2nd time | | 3rd time | |
|---|---|---|---|---|---|---|---|
| function list | | Real part | Imaginary part | Real part | Imaginary part | Real part | Imaginary part |
| Benzene | 0.05 Hz | 3.5016E−03 | −2.4302E−03 | 4.1609E−03 | −4.8505E−03 | 3.0153E−04 | 1.3483E−03 |
| | 0.1 Hz | 3.9524E−03 | −9.3623E−04 | 3.7740E−03 | −2.0834E−03 | 1.9473E−03 | −3.0388E−03 |
| | 0.15 Hz | 1.7843E−03 | −1.1804E−03 | 5.6172E−04 | −3.5881E−03 | 3.0470E−03 | −3.8483E−03 |
| | 0.2 Hz | 3.0718E−03 | −3.0138E−03 | 2.9493E−04 | −6.9185E−03 | −9.7694E−04 | −7.9357E−04 |
| | 0.25 Hz | 4.8622E−04 | −3.5145E−03 | −1.3023E−03 | −1.2159E−03 | 2.9186E−03 | −5.2761E−03 |
| | 0.3 Hz | −3.2781E−04 | −1.1632E−03 | 9.3217E−04 | −9.0421E−04 | 2.3388E−04 | −2.1907E−03 |
| | 0.35 Hz | −1.1271E−04 | −1.2672E−03 | −1.1953E−03 | −5.8861E−04 | −4.4954E−04 | −2.2252E−04 |
| | 0.4 Hz | −1.9811E−04 | −4.1243E−04 | 7.8310E−04 | 1.1616E−03 | −2.0015E−04 | −4.4655E−04 |

TABLE 2-continued

| | | 4th time | | 5th time | | 6th time | |
|---|---|---|---|---|---|---|---|
| | | Real part | Imaginary part | Real part | Imaginary part | Real part | Imaginary part |
| | 0.45 Hz | −3.2110E−04 | −9.5309E−04 | −1.4870E−04 | −2.0256E−03 | −1.3268E−04 | −1.9323E−03 |
| | 0.5 Hz | −6.7475E−04 | −1.6007E−03 | 3.3088E−04 | −2.0037E−03 | −2.1089E−04 | −1.6891E−03 |
| Hexane | 0.05 Hz | 7.9775E−04 | −1.4280E−03 | 4.3121E−03 | −2.7052E−03 | 1.4634E−03 | −2.9216E−05 |
| | 0.1 Hz | 6.9428E−04 | −8.6047E−04 | 8.0318E−04 | −8.0321E−04 | 1.6674E−03 | −1.2698E−03 |
| | 0.15 Hz | 9.1030E−04 | −1.4962E−03 | −6.4128E−04 | −1.8071E−03 | 1.3428E−03 | −9.3388E−05 |
| | 0.2 Hz | 5.4806E−04 | −1.4755E−03 | 9.7325E−04 | −1.6740E−03 | 8.1353E−04 | −1.1253E−03 |
| | 0.25 Hz | 3.3070E−04 | −9.4748E−04 | −1.3007E−03 | −1.8035E−03 | 2.2326E−04 | −1.1962E−03 |
| | 0.3 Hz | −8.1370E−04 | −5.9283E−04 | 5.8612E−04 | −9.9907E−04 | 3.4416E−05 | −7.0743E−04 |
| | 0.35 Hz | 3.5380E−05 | −9.1253E−04 | 7.9799E−05 | −1.0530E−04 | −2.4548E−04 | −7.4378E−04 |
| | 0.4 Hz | −8.6024E−04 | −9.1986E−04 | −1.9932E−04 | −8.6322E−04 | −2.9455E−05 | −2.3609E−04 |
| | 0.45 Hz | −1.0294E−04 | −4.6105E−04 | −6.7466E−04 | −5.2362E−04 | −6.2820E−05 | −4.7822E−04 |
| | 0.5 Hz | −9.4074E−05 | −2.2523E−04 | −1.3762E−04 | 1.9081E−04 | −2.3269E−04 | −5.1153E−04 |

| Transmission | | 4th time | | 5th time | | 6th time | |
|---|---|---|---|---|---|---|---|
| function list | | Real part | Imaginary part | Real part | Imaginary part | Real part | Imaginary part |
| Benzene | 0.05 Hz | 4.9867E−03 | −3.0431E−03 | 2.4297E−05 | −1.3928E−04 | 3.7037E−03 | −3.2796E−03 |
| | 0.1 Hz | −1.5593E−03 | −2.1425E−03 | 4.3840E−03 | −3.1061E−03 | 1.5033E−03 | −1.7290E−03 |
| | 0.15 Hz | 4.3801E−02 | 1.3373E−02 | 3.1079E−03 | −1.8835E−03 | 1.4510E−03 | −2.7317E−03 |
| | 0.2 Hz | 6.9444E−05 | −4.0722E−04 | −3.7567E−04 | −1.8212E−03 | 1.2109E−04 | −2.2364E−03 |
| | 0.25 Hz | 2.8503E−04 | −3.6914E−04 | −9.2118E−04 | −2.9804E−03 | 4.1111E−04 | −1.9790E−03 |
| | 0.3 Hz | −1.5767E−03 | 1.0585E−03 | 1.3683E−03 | 1.3241E−03 | −2.5638E−04 | −1.8561E−03 |
| | 0.35 Hz | 1.9697E−03 | −2.6237E−03 | −7.8711E−04 | −1.9992E−03 | 2.0858E−04 | −1.5888E−03 |
| | 0.4 Hz | 9.3484E−04 | −3.9171E−04 | 3.9877E−03 | 7.9813E−04 | −3.2965E−04 | −1.0577E−03 |
| | 0.45 Hz | −1.1122E−03 | 6.7512E−04 | −8.5908E−05 | −1.1832E−03 | −1.2368E−04 | −7.7181E−04 |
| | 0.5 Hz | 1.0016E−04 | −3.9840E−03 | −2.2968E−04 | −1.5811E−03 | −6.2265E−04 | −1.0820E−04 |
| Hexane | 0.05 Hz | 2.4076E−03 | −5.2604E−04 | 1.5223E−03 | −3.4821E−04 | 1.9397E−03 | −1.5070E−03 |
| | 0.1 Hz | 1.0984E−03 | −1.0577E−03 | 9.7439E−04 | −4.4903E−04 | 7.0359E−03 | −2.0086E−03 |
| | 0.15 Hz | 6.8825E−04 | −9.1890E−04 | 8.2800E−04 | −1.9330E−03 | 3.3088E−03 | −1.7722E−03 |
| | 0.2 Hz | 2.3187E−04 | −1.1415E−03 | −6.5212E−05 | −8.2786E−04 | 4.8914E−04 | −1.1132E−03 |
| | 0.25 Hz | 2.6637E−04 | −8.4200E−04 | 5.4803E−04 | −2.6459E−04 | 1.0928E−04 | −8.2088E−04 |
| | 0.3 Hz | 2.3805E−04 | −7.8988E−04 | −9.0916E−04 | 2.4235E−04 | 3.3331E−05 | −6.0449E−04 |
| | 0.35 Hz | −4.3456E−05 | −6.9875E−04 | 4.1241E−03 | −5.9349E−04 | 1.0571E−04 | −5.6832E−04 |
| | 0.4 Hz | 8.5184E−05 | −8.5807E−04 | −3.1091E−04 | −8.7676E−04 | −1.5905E−04 | −9.4953E−04 |
| | 0.45 Hz | −1.6517E−04 | −4.8740E−04 | 8.8132E−05 | −7.4833E−04 | −2.9430E−04 | −1.1367E−03 |
| | 0.5 Hz | −1.9758E−04 | −3.7404E−04 | −2.6257E−04 | −2.1493E−04 | 2.2764E−04 | 2.0383E−04 |

TABLE 3

| Transmission | | 1st time | | 2nd time | | 3rd time | |
|---|---|---|---|---|---|---|---|
| function list | | Real part | Imaginary part | Real part | Imaginary part | Real part | Imaginary part |
| THF | 0.05 Hz | 2.7090E−03 | −4.5397E−03 | 5.3070E−03 | 4.2905E−03 | 4.7274E−03 | −4.6328E−03 |
| | 0.1 Hz | 1.4656E−03 | −2.9516E−03 | −4.7727E−03 | −1.0230E−03 | 6.6886E−04 | −3.8118E−03 |
| | 0.15 Hz | 4.2306E−04 | −3.2605E−03 | 1.1445E−03 | −1.0521E−03 | 1.9607E−03 | −2.7114E−03 |
| | 0.2 Hz | −3.6275E−04 | −2.1700E−03 | −4.0384E−03 | −6.2671E−03 | 9.3383E−05 | −2.4983E−03 |
| | 0.25 Hz | 8.4755E−05 | −1.8129E−03 | −2.8193E−03 | −1.9578E−03 | 5.8149E−05 | −2.9826E−03 |
| | 0.3 Hz | −9.3758E−04 | −1.2437E−03 | 2.9110E−03 | −7.7523E−03 | −3.8540E−04 | −1.8986E−03 |
| | 0.35 Hz | −4.0817E−05 | −1.5607E−03 | −1.9203E−03 | −2.3355E−03 | −4.2710E−04 | −1.4320E−03 |
| | 0.4 Hz | −1.1797E−04 | −1.2465E−03 | −3.0519E−03 | −4.1162E−03 | −3.7732E−04 | −1.0540E−03 |
| | 0.45 Hz | −4.4283E−04 | −1.0389E−03 | 2.7638E−03 | 1.2716E−03 | −2.2520E−04 | −1.2736E−03 |
| | 0.5 Hz | 4.3644E−04 | 1.2889E−02 | −2.1051E−03 | 3.8618E−03 | −3.5895E−04 | −8.5519E−04 |
| AcOEt | 0.05 Hz | 8.3287E−03 | −6.3745E−03 | 4.7714E−03 | −2.7022E−03 | 4.0144E−03 | −6.8662E−03 |
| | 0.1 Hz | 2.4728E−03 | −4.2155E−03 | 2.8700E−03 | −4.0910E−03 | 8.2954E−03 | −3.5005E−03 |
| | 0.15 Hz | 2.6361E−03 | −5.6555E−03 | 2.0425E−03 | −3.9219E−03 | 8.9336E−04 | −5.6982E−03 |
| | 0.2 Hz | 3.5435E−03 | −1.6972E−03 | 1.6145E−03 | −9.6543E−04 | −3.2510E−03 | −2.6152E−03 |
| | 0.25 Hz | 3.9031E−04 | −2.9082E−03 | −5.5317E−03 | −5.7005E−03 | −3.5862E−05 | −2.9957E−03 |
| | 0.3 Hz | 1.1937E−03 | −1.5939E−03 | 5.1848E−05 | −4.1353E−03 | −1.0936E−05 | −1.6186E−03 |
| | 0.35 Hz | 5.2983E−04 | −2.3053E−03 | −7.1160E−04 | −1.9945E−03 | 1.9694E−04 | −2.8877E−03 |
| | 0.4 Hz | −2.2221E−04 | −1.3395E−03 | 1.1627E−03 | −1.3727E−03 | 2.2312E−04 | −3.0212E−03 |
| | 0.45 Hz | 5.1948E−05 | −1.1326E−03 | 1.2081E−03 | −9.0378E−04 | 5.8500E−04 | −1.4042E−03 |
| | 0.5 Hz | 4.7142E−04 | −6.9413E−04 | 1.4801E−03 | −2.6618E−03 | 2.3259E−04 | −2.7452E−04 |

| Transmission | | 4th time | | 5th time | | 6th time | |
|---|---|---|---|---|---|---|---|
| function list | | Real part | Imaginary part | Real part | Imaginary part | Real part | Imaginary part |
| THF | 0.05 Hz | −4.7801E−03 | 4.4875E−04 | 1.0828E−02 | −3.3315E−03 | 8.2519E−03 | 2.4724E−03 |
| | 0.1 Hz | 7.7380E−04 | −4.9563E−04 | 3.3241E−03 | −7.0858E−03 | 3.7617E−03 | −3.1253E−03 |
| | 0.15 Hz | 1.3026E−03 | −3.4417E−03 | 4.3298E−03 | −4.3408E−03 | 2.3596E−03 | −2.3022E−03 |
| | 0.2 Hz | 8.2172E−04 | −3.8478E−04 | 3.7946E−03 | −3.7410E−03 | 2.6551E−03 | −3.5122E−03 |
| | 0.25 Hz | −3.5614E−05 | −2.8635E−03 | 3.0881E−03 | −7.0124E−04 | −1.0593E−03 | −1.1588E−03 |
| | 0.3 Hz | −5.1604E−04 | −1.1843E−03 | 2.0449E−03 | −4.6688E−03 | 3.5768E−04 | −2.7769E−03 |
| | 0.35 Hz | 8.5193E−04 | 1.2781E−03 | −6.8021E−03 | −7.9326E−03 | 8.5407E−04 | −4.7395E−04 |

TABLE 3-continued

|  | | | | | | | |
|---|---:|---:|---:|---:|---:|---:|---:|
|  | 0.4 Hz | −1.1563E−03 | −3.7994E−04 | 7.5526E−04 | −2.0930E−03 | 9.5509E−04 | −1.3119E−03 |
|  | 0.45 Hz | 2.9824E−04 | −1.3709E−03 | −1.4949E−03 | 2.7081E−05 | −1.5819E−03 | −1.7838E−03 |
|  | 0.5 Hz | −8.2099E−04 | 7.8941E−04 | −6.3080E−04 | 4.3374E−03 | −4.2035E−04 | −2.4177E−04 |
| AcOEt | 0.05 Hz | 4.1241E−03 | −5.2763E−03 | 5.3977E−03 | −4.3981E−03 | 4.8981E−03 | −3.0585E−03 |
|  | 0.1 Hz | 3.1588E−03 | −5.2213E−03 | 3.8915E−03 | −3.9035E−03 | 2.2020E−03 | −4.2108E−03 |
|  | 0.15 Hz | 2.1276E−04 | −5.9911E−03 | 1.5777E−03 | −2.5060E−03 | −1.8568E−02 | −9.3248E−03 |
|  | 0.2 Hz | 1.4753E−03 | −2.5292E−03 | 1.0941E−03 | −3.7257E−03 | −2.3339E−05 | −3.0800E−03 |
|  | 0.25 Hz | 7.6951E−04 | −3.6298E−03 | 8.5740E−04 | −3.3694E−03 | 7.3549E−04 | −3.9929E−03 |
|  | 0.3 Hz | −1.8145E−03 | −5.7200E−04 | −2.1726E−03 | −2.4067E−03 | −5.4469E−04 | −3.0819E−03 |
|  | 0.35 Hz | 6.3538E−05 | −1.7445E−03 | −4.2502E−05 | −2.6269E−03 | 1.3730E−04 | −1.9197E−03 |
|  | 0.4 Hz | 7.1867E−04 | −6.0880E−03 | 8.9617E−04 | −2.8122E−03 | 1.8683E−04 | −8.7831E−04 |
|  | 0.45 Hz | −5.2287E−04 | −1.0210E−03 | 1.7111E−04 | −2.3842E−03 | 8.5005E−03 | −1.4917E−04 |
|  | 0.5 Hz | 5.0477E−05 | −1.1148E−03 | 2.4891E−04 | −1.5040E−03 | −1.8974E−05 | −1.9520E−03 |

Identification of the gas species was performed on the basis of the obtained frequency-domain sensor functions. Principal component analysis (PCA) was performed on the thirty frequency-domain sensor functions (10-dimensional complex vectors), which were obtained from six measurements for each solvent. FIGS. 5(a) and (b) illustrate the results. Note that in FIGS. 5(a) and (b), only the imaginary components of the frequency-domain sensor functions were used because differences between the gas species clearly appear. According to FIGS. 5(a) and (b), the identification of five types of solvent vapors was succeeded by the frequency-domain sensor functions. In the present example, MSS used as the chemical sensor is a type of nanomechanical sensors; a sensor signals are obtained at piezo resistors by detecting induced stress when a receptor layer coated on a sensor device surface absorbs gases and expands (Patent Literature 1 and Non Patent Literature 2). Therefore, a response of the sensor is determined by interactions between the gas and the receptor layer (absorption and desorption of the gas, and the resultant expansion and contraction of the receptor layer, etc.). When multiple gases are measured by using the same MSS, this interaction varies depending on the gas species, and the frequency-domain sensor functions accordingly changes, enabling the identification of gas species based on the frequency-domain sensor function.

To identify a species of a sample, first the aforementioned measurement and principal component analysis are performed beforehand, and then a coordinate space composed of several principal components is divided into a cluster to which each gas type belongs with high possibility. For example, in an example of the result of the principal component analysis illustrated in FIGS. 5(a) and (b), the 2-dimensional space composed of the first principal component PC1 and the third principal component PC3 is divided into the clusters to which the five solvents belong. A sample to be identified is measured in the same way to obtain the frequency-domain sensor function. Then, this frequency-domain sensor function (specifically, a vector including the values of a sensor function of each frequency point as shown in the above table) is converted to a value for each principal component obtained in the previously performed principal component analysis, and the gas species of the sample can be identified according to the previously obtained clusters with a set of the values of these principal components. Note that it is obvious how the value of each principal component of the sample can be converted from each component of the above vector, that is the frequency sensor function of the sample, from the result of the previously performed principal component analysis, so that further description is omitted.

It should be noted here that in the above example, the flow rate of MFC1 10 was randomly changed to provide white noise as the input instead of an impulse in order to obtain the frequency-domain sensor function. However, the input $x_i(t)$ does not need to randomly change as long as the input contains the frequency component in the predetermined range. Here, considering the upper limit of the frequency component, "predetermined frequency component" does not need to contain a high frequency component which is not substantially transferred in the system, as the targeted system of the present invention has a low-pass filter-like property (a cut-off frequency is about 1 Hz in the above example). Furthermore, as the measurement is performed only for a finite period of time (for 20 seconds in the above example), a lower limit of the frequency component is determined by a measurement period of time. For example, as seen from the description of the above example, the range of the frequencies included in the input is from 0.05 Hz to 0.5 Hz. In addition, if desired precision can be achieved even in a narrower frequency range, the range of the frequency components to be contained in the input can be also narrower. Needless to say, a broader frequency range can be used if the precision improves depending on conditions.

Next, the analysis was performed with a different technique by using the same measurement data. For a discrete time function of Equation (1), a discrete time finite response sensor function (a discrete time finite impulse response function) is given in the following equation.

$$y(t_i) = \sum_{j=0}^{p} c(\tau_j) x(t_i - \tau_j) \quad [\text{MATH. 3}]$$

Here, $\Delta t$ is a sampling time interval and satisfy $\tau_j = \Delta t \times j$ and $h(\tau) = c(\tau_j) \Delta t$. With respect to the observed time series $x(t_i)$ and $y(t_i)$ (which correspond to an input $x(t)$ and an output $y(t)$, respectively), in which i=1, 2, . . . , n. Least squares fitting is performed so that the sum of square errors between both sides of these equations become minimum to obtain a coefficient vector of the discrete time finite response sensor function, i.e., $C = [C(0), \ldots C(\tau_p)]$. As $\Delta t = 0.05$ seconds and p=19, C was calculated from the measurement data for 20 seconds for the six measurements of the five solvents ($H_2O$, EtOH, AcOEt, benzene and hexane). Furthermore, principal component analysis was performed by using C of all these 20-dimensional vectors as data. FIGS. 6(a) and (b) illustrate data plotted on the principal component plane consisting of the first and the second principal components. As illustrated in FIGS. 6(a) and (b), measurement results on the principal component plane are separated from each other, leading to the identification of gas species. Similar to the previously described frequency sensor function, the coefficient vector C of the discrete time finite response sensor function is converted to a value of each principal component which is obtained by the previously performed principal component analysis, and the gas species of the sample can be identified by determining the cluster to which the set of values of these principal components belongs according to the previously obtained values.

Example 2

(Identification of the Concentration Based on Sensor Functions)

In the present example, water vapors (the head space gas of water) at different concentrations were measured by using a membrane-type surface stress sensor (MSS), and the gas concentration was identified.

Measurement was performed by using the same experimental system used in Example 1; MFC was controlled to supply a head space gas 70 of water to the sensor chamber 60 in which the MSS coated with PMMA was set. In the present example, as illustrated in FIG. 7(a), an experiment was carried out with two patterns of gas flow rates; MFC1 10 were set at 5 sccm (a specific saturated vapor concentration of 5%) and 95 sccm (a specific saturated vapor concentration of 95%) with a randomly changing component at every second (1 Hz) in a range of −5 to +5 sccm. Furthermore, a flow rate of MFC2 20 was controlled so that the sum of the flow rates of MFC1 10 and MFC2 20 was always 100 sccm. FIG. 7(b) illustrates the responses of the sensor.

Figure 8:
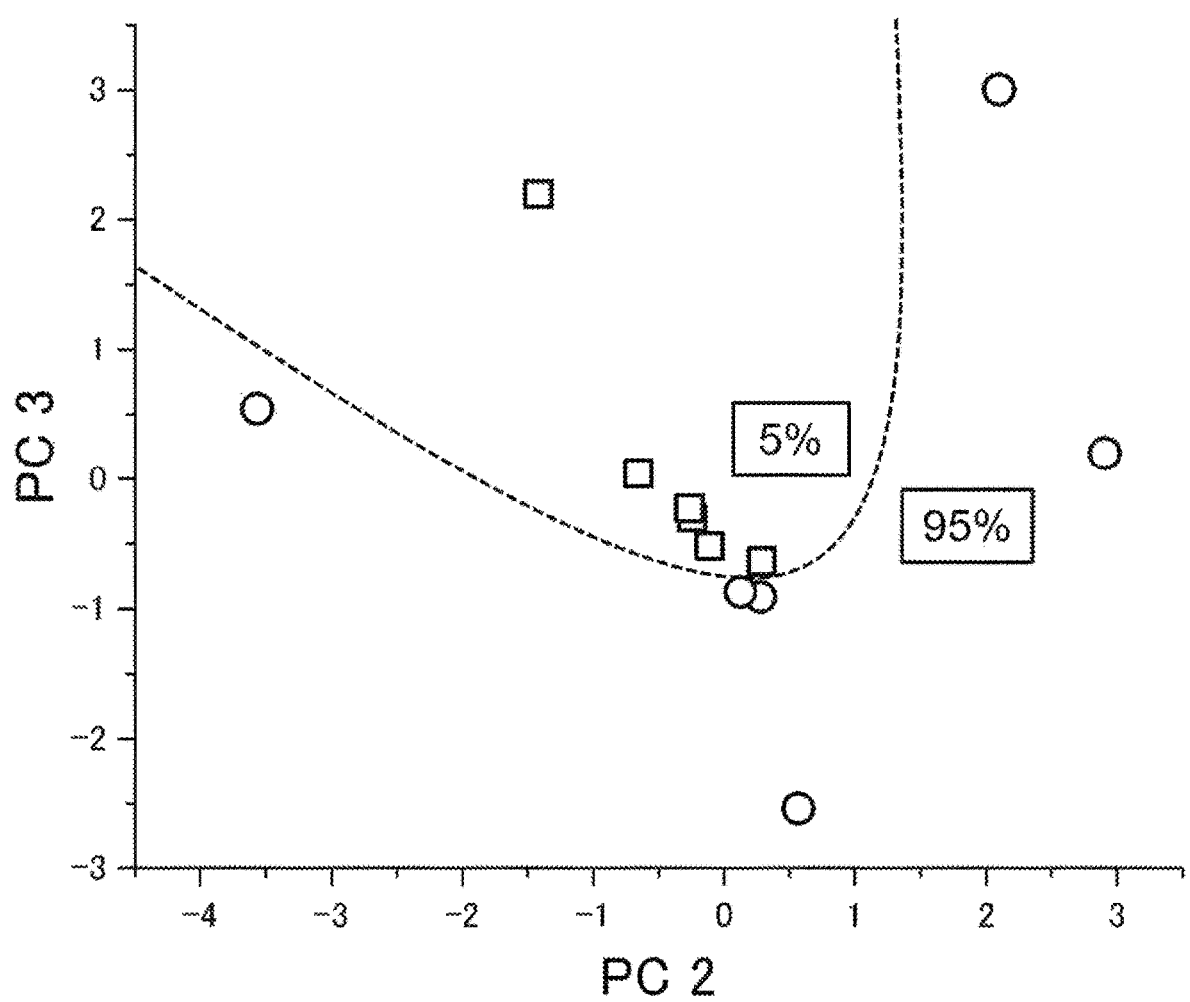
FIG. 8 is the result of principal component analysis performed on the sensor functions obtained from each measurement in Example 2.

A frequency-domain sensor function was obtained by the same technique as the one used in Example 1, and analysis was performed by PCA. As illustrated in FIG. 8, the result shows that it was possible to distinguish between the measurement results the concentration ratio of which are 5% and 95%. This indicates that the identification of the gas concentration is possible by using the frequency-domain sensor function. When the response of the sensor is linear with respect to the gas concentration, the frequency-domain sensor functions are identical regardless of the gas concentration; hence, identification based on the concentration cannot be performed. Although the concentration ratio fluctuated from 0% to 100% in Example 1, the response was substantially linear with respect to the concentration. Thus, the identification based on a gas type and a temperature was possible regardless of the concentration. However, the response of the sensor is often non-linear with respect to the concentration in the high concentration region, and the sensor function may differ between a low concentration and a high concentration. In the present example, the measurements were performed at largely different two concentration regions: 5±5% and 95±5%. Thus, it was possible to distinguish the concentrations according to the difference in the frequency-domain sensor functions due to the concentrations.

Example 3

(Identification of Temperature Based on Sensor Function)

In the present example, water vapors (head space gas of water) at different temperatures were measured by using a membrane-type surface stress sensor (MSS), and the temperature was identified.

Figure 9:
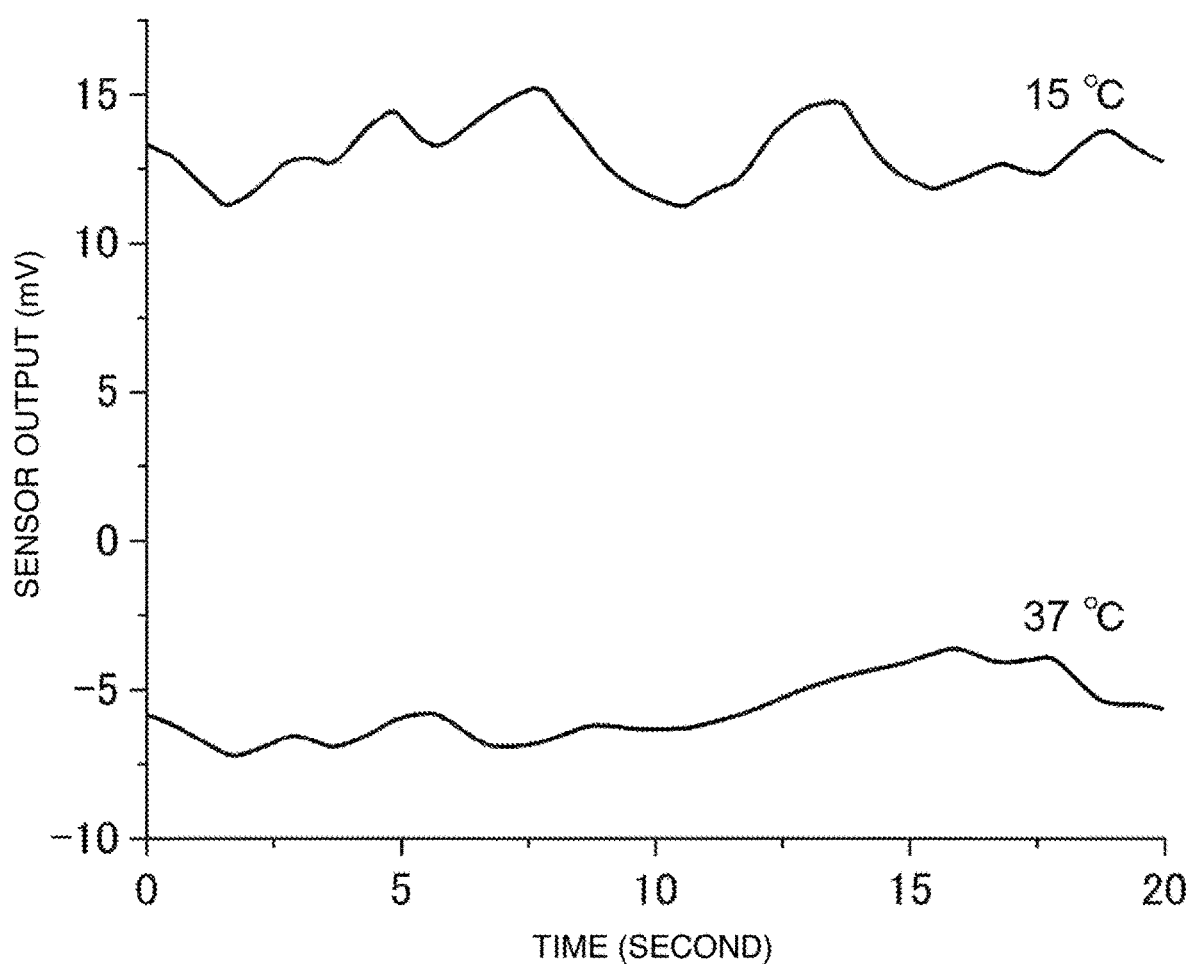
FIG. 9 is sensor signals for the measurements of water vapor at different temperatures in Example 3.

The same experimental system as in Example 1 was used; MFC was controlled to supply a head space gas 70 of water to a sensor chamber 60 in which the MSS coated with PMMA was set, and measurements were performed. As performed in Example 1, a flow rate of MFC1 10 was randomly changed at every second (1 Hz) in a range of 0 to 100 sccm, and a flow rate of MFC2 20 was controlled so that a sum of the flow rates of MFC1 10 and MFC2 20 was always 100 sccm. In the present example, the temperature of an incubator 80 was set at 15° C. and 37° C., and the measurements were performed. FIG. 9 illustrates the responses of the sensor.

Figure 10:
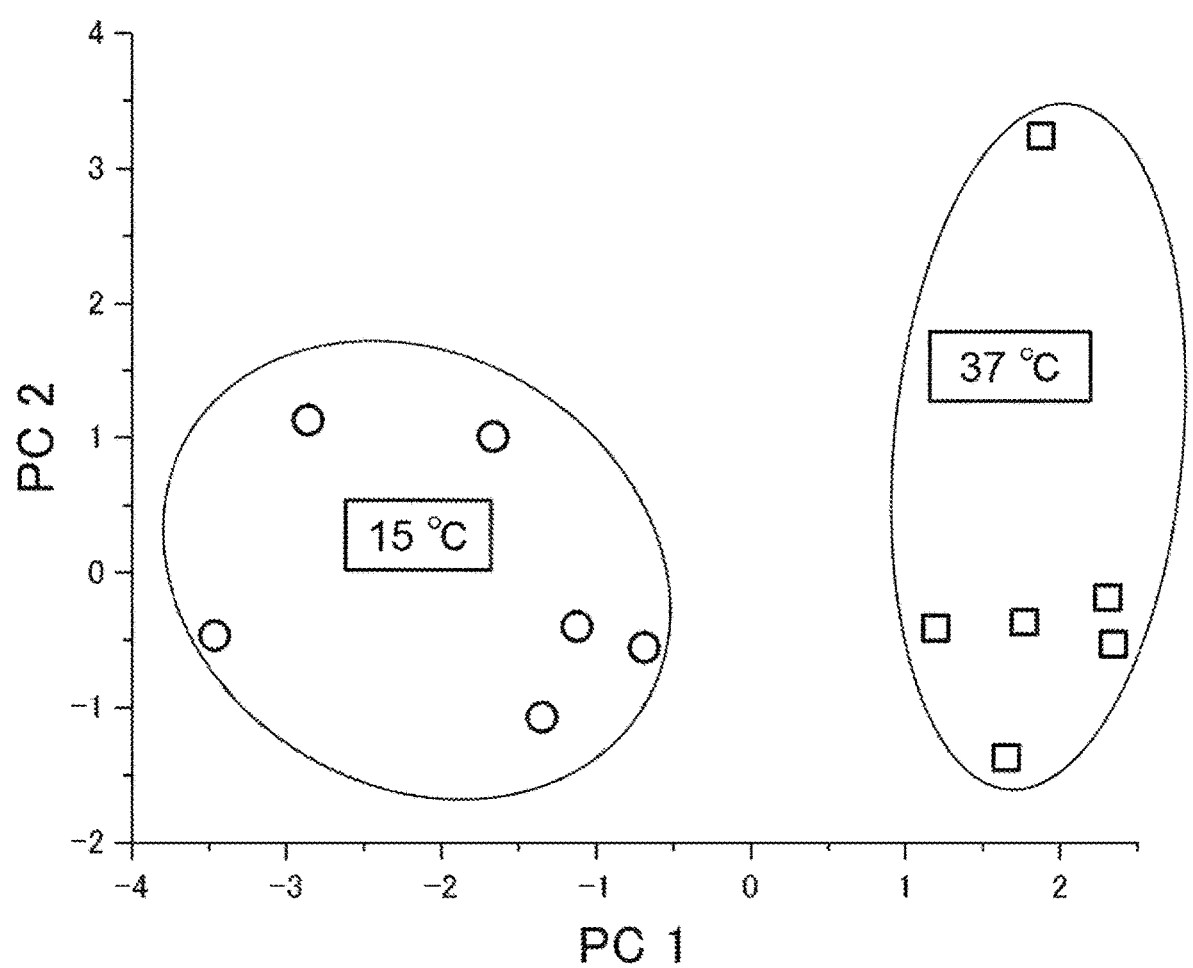
FIG. 10 is the result of principal component analysis performed on the sensor functions obtained at each measurement in Example 3.

Frequency-domain sensor functions were obtained by the same method used in Example 1, and analysis based on PCA was performed. The result shows that it was possible to identify measurement results at 15° C. and 37° C. as illustrated in FIG. 10. This indicates that the identification of the gas temperature is possible by using the frequency-domain sensor function. In the MSS, the sensor response is affected by gas absorption and desorption in a receptor layer and the resultant expansion and contraction of the receptor layer. As such a phenomenon is influenced by the temperature, the sensor function varies when the temperature changes, leading to the identification of the temperature.

In the present example, estimation using the frequency components up to 1 Hz—twice as high as the Nyquist frequency—results in higher precision than the one using the frequency component up to 0.5 Hz, that is the Nyquist frequency. As the flow rate changed at 1 Hz, in principle, the frequency components higher than 0.5 Hz—the Nyquist frequency—does not contribute to the estimation of the input (the flow rate of MFC1) based on the frequency-domain sensor function. However, the frequency components which are higher than the Nyquist frequency can contribute because of a nonlinear effect of the sensor. Therefore, there is a case where the input can be estimated more precisely by evaluating the sensor function including the frequency components higher than the Nyquist frequency. However, when much higher frequency components are included in calculating the frequency-domain sensor functions for the estimation of the input, the high frequency components may excessively contributes, resulting in worse precision.

INDUSTRIAL APPLICABILITY

As described above, according to the present invention, a sensor function is calculated based on the relationship between the gas supply considered as an input and a sensor signal response considered as an output for a gas measurement by using chemical sensors, leading to gas analysis. Thus, when the input and the output are known, the analysis is possible with any chemical sensor. Furthermore, even in the case where the flow rate of a sample to be supplied to the sensor is not precisely controlled, the sample analysis becomes possible when the flow rate considered as the input or change of the concentration is known. For example, for applications where samples are supplied to a sensor by MFCs or pumps, the sample supplying method can be replaced with a simple one that uses a blower, a syringe and so on (however, the flow rate is needed to be monitored with a tool including a flow meter). In addition, when a sensor function is calculated beforehand for a system to which chemical sensors are adopted, monitoring of the flow rate or the concentration from sensor signals become possible. The present invention makes it possible to analyze a sample only with a small measurement system without a bulky device, and no strict control for the sample introduction is required. Therefore, the present invention can be applied to on-site analysis in the fields of food, environment, medicine, for example.

REFERENCE SIGNS LIST

100 Experiment system
10 Mass flow controller (MFC) 1
20 Mass flow controller (MFC) 2
30 Solvent
40, 50 Vial
60 Sensor chamber
70 Head space gas
80 Incubator

The invention claimed is:

1. A sample identification method by means of a chemical sensor measurement, comprising:
   supplying a time-varying amount of an unknown sample to a chemical sensor,
   measuring a time-varying response from the chemical sensor,
   deriving a sensor function of the chemical sensor on the unknown sample based on the time-varying amount of the unknown sample provided to the chemical sensor and the time-varying response from the chemical sensor, wherein the sensor function is a transfer function that takes the time-varying amount of the unknown sample as an input and transfers the input to a sensor signal for describing a relation between the time-varying amount of the unknown sample and the time-varying response from the chemical sensor, and
   identifying the unknown sample based on the sensor function.

2. The sample identification method by means of the chemical sensor measurement according to claim 1, wherein identifying the unknown sample based on the sensor function includes comparing the sensor function of the unknown sample with a sensor function of one or more known samples, wherein the sensor function of the one or more known samples are obtained separately.

3. The sample identification method by means of the chemical sensor measurement according to claim 1, wherein a variation range of the time-varying amount of the unknown sample supplied to the chemical sensor is limited to a predetermined range.

4. A sample identification device which performs identification of a sample input by using the sample identification method by means of the chemical sensor measurement according to claim 1, the device comprising:
   means for supplying the time-varying amount of the unknown sample to the chemical sensor.

5. The sample identification method by means of the chemical sensor measurement according to claim 1, wherein the sensor function is a time-basis sensor function.

6. The sample identification method by means of the chemical sensor measurement according to claim 5, wherein the time-basis sensor function is obtained by fitting the sensor function so that convolution of the sensor function and the time-varying amount of the unknown sample approximates the measured response from the chemical sensor.

7. The sample identification method by means of the chemical sensor measurement according to claim 1, wherein the sensor function changes in accordance with at least one property of the unknown sample.

8. The sample identification method by means of the chemical sensor measurement according to claim 7, wherein the property of the unknown sample is species, concentration, temperature, or pressure.

9. The sample identification method by means of the chemical sensor measurement according to claim 1, wherein the sensor function has a basis which is transformed into another basis other than time.

10. The sample identification method by means of the chemical sensor measurement according to claim 9, wherein the transformation of the basis is performed by orthogonal transformation or pseudo-orthogonal transformation.

11. The sample identification method by means of the chemical sensor measurement according to claim 10, wherein the orthogonal transformation or the pseudo-orthogonal transformation is a transformation that transforms convolution into multiplication.

* * * * *